United States Patent [19]

Hedrick

[11] 4,020,555

[45] May 3, 1977

[54] CONNECTING MECHANISM FOR A SAW BLADE

[75] Inventor: John R. Hedrick, La Crescenta, Calif.

[73] Assignee: Pevrick Engineering Co., Inc., Sun Valley, Calif.

[22] Filed: Apr. 12, 1976

[21] Appl. No.: 675,924

[52] U.S. Cl. .............................. 30/392; 128/317; 279/89; 145/35 E
[51] Int. Cl.² ..................................... B27B 19/09
[58] Field of Search ........... 30/335, 337, 392, 393, 30/394; 279/81, 89, 91, 1 B; 128/317; 145/31 R, 35 E

[56] References Cited

UNITED STATES PATENTS

| 44,823 | 10/1864 | Rose | 279/81 |
| 1,064,493 | 6/1913 | Kropat | 279/81 |
| 1,413,101 | 4/1922 | Cushing | 279/89 |
| 3,823,473 | 7/1974 | Hoffman | 30/392 |

*Primary Examiner*—Al Lawrence Smith
*Assistant Examiner*—J. C. Peters
*Attorney, Agent, or Firm*—Robert E. Geauque

[57] ABSTRACT

A connecting mechanism for a saw blade of a surgical cutting tool in which the blade has two side projections spaced slightly from one end thereof and in which the connecting mechanism comprises a rotatable collar on the end of a reciprocating shaft which moves the blade; the end of the shaft and collar having slots alignable to receive the blade and the collar having pockets to receive the projections when the collar is released to rotate to a blade moving position.

12 Claims, 6 Drawing Figures

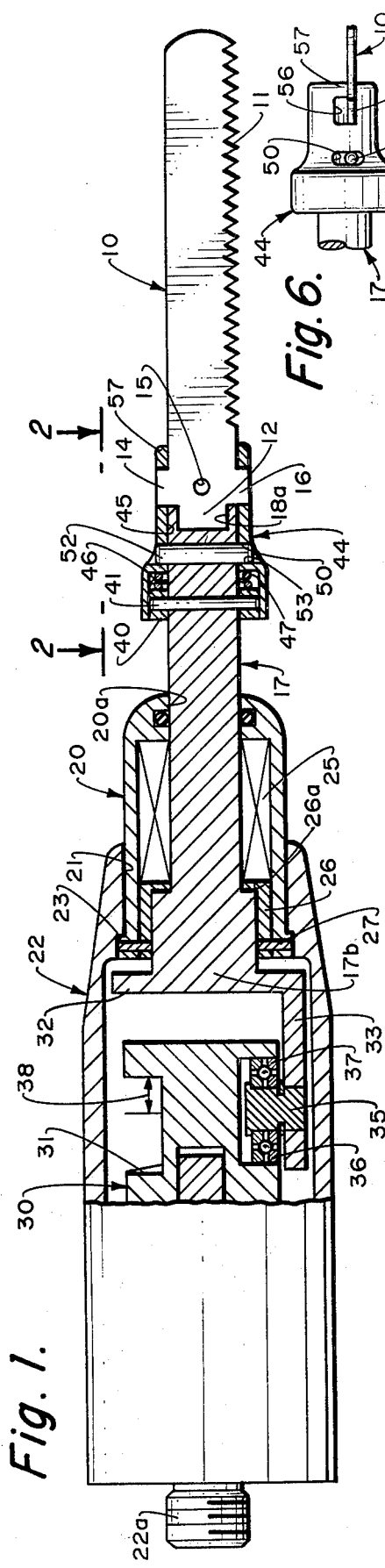
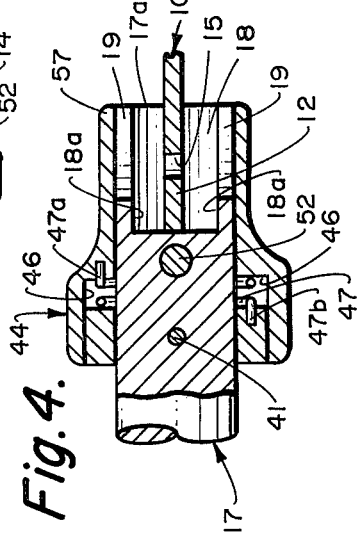
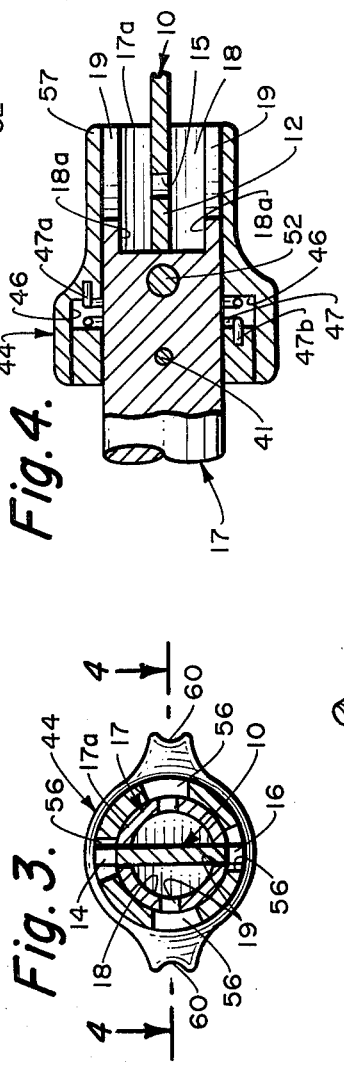
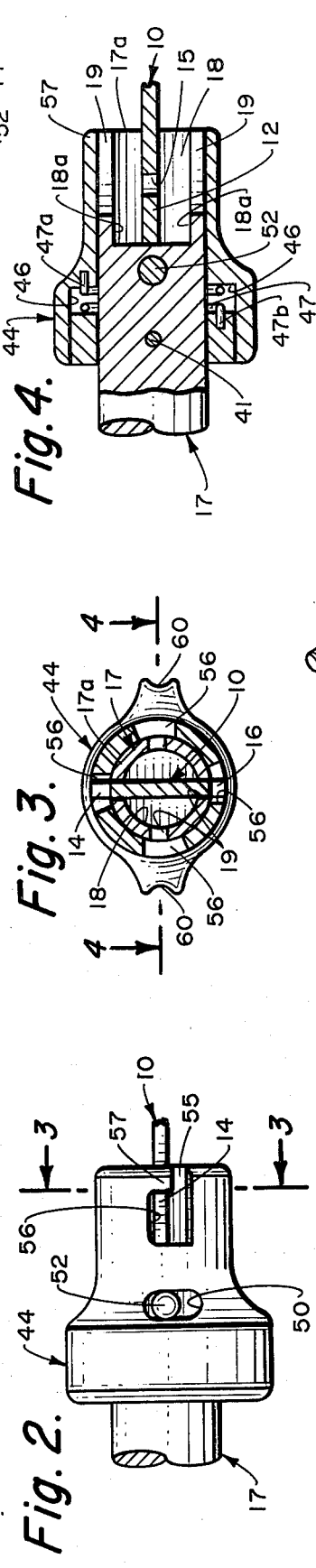
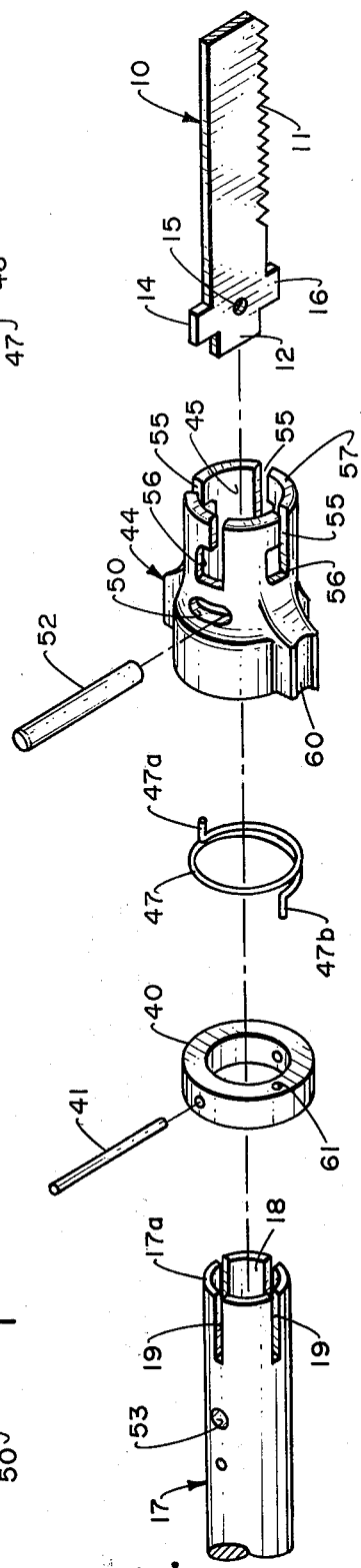
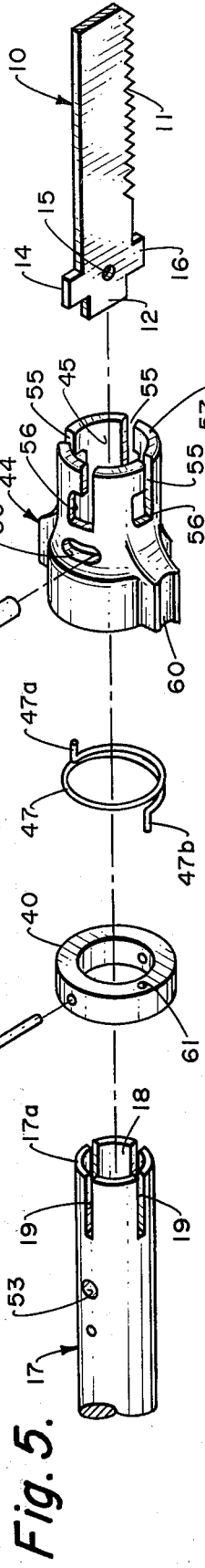

CONNECTING MECHANISM FOR A SAW BLADE

BACKGROUND OF THE INVENTION

For orthopedic and other surgery, the surgeon utilizes a reciprocating saw which is attached to the end of a shaft which is reciprocated by the rotation of an air turbine. The shaft is supported in a hand held casing and the saw blade is attached to the end of the shaft exteriorly of the casing. Various means have been utilized for connecting the saw blade to the end of the reciprocating shaft. For instance, the blade can have a depression which receives a spring biased ball detent carried in a pocket. In another attachment, the blade is inserted into a socket and secured therein by a set screw which requires a wrench to fasten the saw in the end of the reciprocating arm.

Usually, the blade is heat treated for strength after the teeth have been cut and the heat treatment must be done before any fastening member is attached to the blade since, in most cases, the fastening member would not withstand the heat treatment. With most connections, it is necessary to utilize two hands to release a blade because of the fact that either a wrench or some other type of relative movement must be imparted to the fastening section. Blades attached to the reciprocating arm can be of various lengths and various thicknesses as required for different operations.

SUMMARY OF THE INVENTION

The present invention provides a saw blade and connecting mechanism for connecting the blade to a reciprocating shaft. The saw blade is made of a solid piece of steel without any special attachments or projections welded to it for purposes of connection to the recirporcating arm and is therefore easily fabricated and heat treated. Also, no tools or accessories are required to make the connection of the blade. The end of the saw blade is located in a socket in the end of the shaft and is secured in place by a rotatable locking collar on the end of the shaft. Slots are located in the end of the shaft and in the collar and the slots can be aligned in one rotating position of the collar. The end of the saw blade fits within the socket and has outward projections on opposite sides spaced slightly from the end of the blade. When the slots are aligned, the projections can move through the slots to place the end of the blade in the socket. The slots in the collar are enlarged to form pockets for receiving the projections when the collar is rotated after insertion of the saw blade. This rotation of the collar locks the projections to the reciprocating shaft and maintains the end of the saw blade in the socket in the end of the shaft. Thus, rotation of the blade relative to the shaft is prevented by the slots in the end of the reciprocating shaft and cocking or angular movement of the blade relative to the shaft is prevented by the socket in the end of the shaft and by the sides of the collar and the collar locks the saw to the shaft for reciprocating movement.

The collar is spring biased to the locking position and the complete cutting instrument can be held in one hand and the collar can be easily rotated by the fingers of the hand into position for alignment of the slots to either remove or attach a blade to the reciprocating shaft. No tools or accessories are necessary to remove or change a blade and the blade is locked in position by simply releasing the collar. The projections on the saw blade are an integral part of the blade and the complete blade can be heat treated without any attention to special locking features. Also, the blade will not be discolored after heat treatment by welding parts to the blade to form a connection of the blade to the shaft.

BRIEF DESCRIPTION OF THE DRAWINGS

FIG. 1 is a side elevational view partly in section showing the cam mechanism for reciprocating the shaft and saw blade attached to the end of the shaft;

FIG. 2 is a plan view along line 2—2 of FIG. 1 showing the locking collar in position to hold the blade;

FIG. 3 is a vertical section along line 3—3 of FIG. 2 illustrating the saw blade in the slots in the end of the shaft;

FIG. 4 is a horizontal section along line 4—4 of FIG. 3 illustrating the spring for biasing the collar to locking position;

FIG. 5 is an expanded perspective view of the blade and the parts of the connecting mechanisms; and FIG. 6 is a plan view similar to FIG. 2 showing the collar in position to release or insert the blade.

BRIEF DESCRIPTION OF THE SHOWN EMBODIMENT

Saw blade 10 has teeth 11, a reduced end 12 and side projections 14 and 16 adjacent end 12. An opening 15 in the blade facilitates storage of the blade. The blade 10 is connected to end 17a of reciprocating shaft 17 which contains a socket 18. Four slots 19 are located in the wall of socket 18 outwardly from closed end 18a of the socket. A nose section 20 is secured in end opening 21 of tool housing 22 and is positioned by step 23 in the end opening 21. Shaft 17 extends through opening 20a in the nose section 20 and through linear ball bearings 25 in the nose section which support shaft 17 for reciprocating movement; one such bearings being designated Bardon LS6X200. Shaft 17 has enlarged end 17b which reciprocates in a bronze bushing 26 secured in the nose section by pin 27. A flange 26a on the bushings positions one end of bearings 25. Both the bushing 26 and the enlarged shaft end 17b are square in cross section to prevent rotation of shaft 17 relative to housing 22.

An air turbine (not shown) is located in housing 22 and is driven by high pressure air from connection 22a for rotating cam member 30 containing sinusoidal shaped groove 31. A flange 32 is attached to the enlarged end shaft 17b and connects with arm 33 which extends into the casing 22 along cam member 30. A post 35 projects from arm 33 into groove 31 and supports cam follower 36 on ball bearings 37. The turbine rotates the cam member 30 which in turn causes the arm 33 and shaft 17 to reciprocate back and forth, thereby reciprocating the saw blade. The stroke of the blade is determined by the displacement of groove 31 as shown in FIG. 1 by line 38.

A ring 40 is secured to shaft 17 by means of a pin 41 which passes through the ring and through a hole in the shaft. Locking collar 44 has an opening 45 for receiving shaft end 17a and an enlarged end opening 46 providing a recess for receiving ring 40 and a coil spring 47 located around shaft 17. The collar 44 contains two opposed elongated openings 50 (see FIG. 2). A pin 52 extends through opening 53 in shaft 17 and the ends of the pin project into elongated openings 50. Spring 47 has one end 47a inserted in a hole in collar 44 and the other end 47b inserted in a hole in ring 40 (see FIG. 4). The locking collar 44 is rotatable on shaft end 17a and spring 47 biases the collar counterclockwise as viewed from the end of the shaft so that pin 52 normally engages one side of each opening 50.

Four equally spaced slots 55 are located in collar 44 and each slot connects with a pocket 56 which is long enough to receive one of the projections 14, 16 on the saw blade 10. However, the bottom of pockets 56 is curved to prevent projections 14, 16 from engaging the bottom of the pocket. When collar 44 is rotated clockwise against spring 47 to its first angular position, the slots 55 in the collar can be aligned with the slots 19 in the end of shaft 17 (see FIG. 6). Thereafter, a first set of slots comprising any two opposed slots 19 in the shaft will receive the edges of the saw blade and the corresponding aligned slots 55 (second set) in the collar will receive the blade projections 14, 16. The blade can then be inserted until end 12 of the saw blade is located in the closed end 18a of socket 18. When the collar 44 is released, it will rotate and return to its second angular position of FIG. 2 and the projections 14, 16 on the blade will enter two pockets 55. In the second position, the curved bottom of pockets 56 prevent the projections 14, 16 from engaging the bottom and prevent the collar from returning to its normal position. Therefore, spring force means on the projections 14, 16 in a direction toward the bottom of the pocket and this force compensates for manufacturing tolerance in the width of the projections and enables the use of various thicknesses of blades. If the projections are too narrow, relative longitudinal movement could occur between the collar pockets and the projections resulting in axial play of the blade. During rapid oscillations of the blade, such play could damage the blade. However, the device is operative for a considerable period of time should the projections 14, 16 be maneuvered enough to engage the bottom of the pocket; the position at which the projections engage the pockets under spring force being referred to herein as the second position. Edge portions 57 of the collar 44 defining slots 55 overlap the projections 14, 16 when located in pockets 56 so that longitudinal movement of shaft 17 will be imparted to the saw blade 10 by pin 52 and collar 44 when the collar is released, and the blade projections are in two pockets 56.

The collar 44 has side projections 60 which can be engaged by the fingers to rotate the casing clockwise against the spring 47 until the pin 52 engages the opposite side of opening 50. It is understood that only one pair of slots in the shaft and collar will be in use at one time and the second pair of slots are provided so that the user may select any one of four cutting directions of the saw blade. Since two sides of the blade are snugly received by slots 19 in the shaft, the blade cannot rotate relative to the shaft during reciprocation of the shaft. Also, since the end 12 of the blade is snugly received in closed end 18a of the socket 18 and since two portions 57 engage opposite edges of the blade, the blade cannot become cocked by up or down movement relative to the shaft during reciprocation of the shaft. The portions 57 serve to pull the blade back and forth at the end of the shaft and there is no tendency for the collar to release the blade because there is no force to cause rotation of the collar. Using projection 60, it is possible to rotate the locking collar with the same hand that is holding the cutting tool in order to release the blade and insert another blade quickly with the other hand. It is apparent that the blade 10 and projections can be fabricated of the same material and can all be heat treated at the same time and there are no additional pieces that have to be added to the blade in order to provide an attachment to the end of the reciprocating shaft.

What is claimed is:

1. In combination:
a reciprocating shaft;
means for releasably mounting a tool on one end of said shaft;
said mounting means comprising a collar mounted exteriorly on said one end of said shaft for limited rotation between first and second angular positions;
a socket on said one end of said shaft for receiving one end of said tool; at least one slot in said collar;
at least one projection on said one end of said tool movable through said slot when said collar is in said first position; and
a pocket in said collar in communication with said slot for receiving said projection when said collar is in said second position;
said pocket transmitting the reciprocation of said shaft to said tool.

2. In the combination as defined in claim 1:
means for biasing said collar into said second position to maintain said projection in said pocket during reciprocation of said shaft.

3. In the combination as defined in claim 1:
at least one pin projecting from a side of said shaft and an elongated opening in said collar receiving said pin.

4. In the combination as defined in claim 2 wherein:
said biasing means comprises a coil spring surrounding said one end of said shaft and having its ends fixed to said shaft and said collar.

5. In the combination as defined in claim 1:
said socket having a wall containing at least one slot for receiving an edge of said one end of said tool for preventing rotation of said tool relative to said shaft when said tool is in said socket.

6. In the combination as defined in claim 1:
said socket having a closed end beyond said slots;
said tool having a reduced end portion beyond said projection, said reduced end portion being received by said closed end of said socket when said tool is in said socket.

7. In combination:
a saw blade having two side projections from opposite edges at one end of said blade;
a reciprocating shaft;
a collar mounted about one end of said shaft for limited rotation between first and second angular positions;
a socket in said one end of said shaft;
a first set of slots comprising at least two opposite slots in the wall of said socket and a second set of slots comprising at least two opposite slots in the wall of said collar;
said slots in said socket and said collar being in alignment when said collar is in said first angular position; and
a pocket connected with each slot in said collar for receiving one of said projections when said collar is in said second angular position;
said projections being inserted into both sets of slots and the edges of said one end of said blade being inserted only into said first set of slots in said socket when said collar is in said first position and said pockets moving to receive said projection when said collar moves into said second position to thereby secure said saw blade to said shaft.

8. The combination as defined in claim 7:

means for biasing said collar into said second angular position to maintain said projections in said pockets during reciprocation of said shaft.

9. In the combination as defined in claim 7:

said projection being spaced from one end of said blade having a reduced width;

said first set of slots in said socket terminating short of the end of said socket to form a closed end of said socket;

said reduced end being inserted into said closed end when said projections are in said pockets.

10. In the combination as defined in claim 8:

at least one pin projecting from a side of said shaft and an elongated opening in said collar receiving said pin, the bottom of said pockets being curved ot be narrower than said projections so that said projections engage said pockets before said pin engages an end of said elongated opening in order to maintain a biasing formed between said collar and said projections.

11. In the combination as defined in claim 8 wherein said biasing means comprises a coil spring surrounding said one end of said shaft and havings its end fixed to said shaft and said collar.

12. In the combination as defined in claim 7 wherein each of said pockets comprises an enlargement of one of said slots of said second set in said collar;

said projections being retained in said pockets by a edge portion of said collar defining said second set of slots.

* * * * *